(12) United States Patent
Ritter et al.

(10) Patent No.: US 9,370,533 B2
(45) Date of Patent: Jun. 21, 2016

(54) WOUND HEALING COMPOSITIONS COMPRISING MICROSPHERES

(71) Applicant: POLYHEAL LTD., Yavne (IL)

(72) Inventors: Vladimir Ritter, Kiriat Yam (IL); Mery Kleyman, Tel Aviv (IL); Deborah Hanah Bartfeld, Mazkeret Batia (IL); Eilon Asculai, Lehavim (IL)

(73) Assignee: PolyHeal Ltd., Yavne (IL)

( * ) Notice: Subject to any disclaimer, the term of this patent is extended or adjusted under 35 U.S.C. 154(b) by 0 days.

(21) Appl. No.: 14/427,747

(22) PCT Filed: Sep. 12, 2013

(86) PCT No.: PCT/IL2013/050774
§ 371 (c)(1),
(2) Date: Mar. 12, 2015

(87) PCT Pub. No.: WO2014/041543
PCT Pub. Date: Mar. 20, 2014

(65) Prior Publication Data
US 2015/0231170 A1    Aug. 20, 2015

Related U.S. Application Data

(60) Provisional application No. 61/700,362, filed on Sep. 13, 2012.

(51) Int. Cl.
| | |
|---|---|
| *A61K 9/16* | (2006.01) |
| *A61L 26/00* | (2006.01) |
| *A61K 31/745* | (2006.01) |
| *A61P 17/02* | (2006.01) |
| *A61K 47/10* | (2006.01) |

(52) U.S. Cl.
CPC .............. *A61K 31/745* (2013.01); *A61K 9/16* (2013.01); *A61K 9/1617* (2013.01)

(58) Field of Classification Search
CPC ............ A61L 26/0014; A61K 31/745; A61K 31/765; A61K 9/16; A61K 9/1617
USPC ........................................ 424/501, 422, 489
See application file for complete search history.

(56) References Cited

U.S. PATENT DOCUMENTS

| | | | |
|---|---|---|---|
| 5,861,149 A | 1/1999 | Ritter | |
| 6,086,863 A | 7/2000 | Ritter et al. | |
| 7,465,463 B2 | 12/2008 | Ritter et al. | |
| 2003/0008893 A1* | 1/2003 | Colon-Cruz | C07D 487/04 514/300 |
| 2009/0083867 A1* | 3/2009 | Ferguson | A61K 31/70 800/3 |

FOREIGN PATENT DOCUMENTS

| | | |
|---|---|---|
| WO | 9614094 A1 | 5/1996 |
| WO | 9855108 A1 | 12/1998 |
| WO | 0024378 A1 | 5/2000 |

OTHER PUBLICATIONS

Alkar ("Sodium Chloride Brine Tables for 60 F (15.5 C)", 2 pages, accessed on Sep. 30, 2015 from http://www.alkar.com/download/pdf/Sodium%20Chloride%20Brine%20Tables%20for%2060F.pdf).*
Chemicalland21 (http://chemicalland21.com/industrialchem/organic/POLYETHYLENE%20GLYCOL.htm, accessed on Sep. 30, 2015, 3 pages).*
Govrin et al., "New method for treating hard-to-heal wounds: clinical experience with charged polystyrene microspheres." Wounds uk 6:4 : 52-61 (2010).

* cited by examiner

*Primary Examiner* — Alma Pipic
(74) *Attorney, Agent, or Firm* — Winston & Strawn LLP (57) ABSTRACT

Pharmaceutical or medical compositions for treating a wound are provided, the composition comprise microspheres as an active ingredient and water as a carrier for said microspheres. In some embodiments, compositions comprising a thickening agent dissolved within the water to form a solution having a specific gravity similar to that of the microspheres are provided.

17 Claims, 4 Drawing Sheets

WOUND HEALING COMPOSITIONS COMPRISING MICROSPHERES

FIELD OF THE INVENTION

The present invention is directed to the field of wound healing. In particular, the invention is directed to improved compositions comprising microspheres for treating wounds and methods for manufacturing same.

BACKGROUND OF THE INVENTION

Chronic and hard to heal wounds represent a significant burden to patients, health care professionals, and the health care system, affecting in the United States alone nearly 6 million patients and costing an estimated 20 billion dollars annually. Individuals with underlying disease tend to suffer from chronic wounds, and impaired wound healing is a hallmark of a variety of medical conditions.

Normally, wound healing processes are composed of the following steps: (1) vascular response (hemostasis); (2) inflammatory response (inflammation); (3) a proliferative phase (granulation, epithelialization) also known as the active growth phase; and (4) a maturation phase (reconstruction phase). The duration, efficiency and order of the wound healing stages may be disturbed, thus leading to a chronic wound. A number of exogenous and endogenous factors, as well as a variety of medical conditions may cause such disturbance. Examples of such factors include infections, ulceration, circulation disorders, malnutrition, stress, cancer radiotherapy and/or chemotherapy, aging and trauma.

U.S. Pat. Nos. 5,861,149 and 6,086,863, to an inventor of the present application, relate to a composition and a method for treating a wound consisting essentially of an agent being capable of forming a multi-point contact with a cellular membrane, said agent being substantially non-biodegradable during the period of treatment. In particular embodiments, the agent is microspheres made of non-biodegradable polymer (e.g., polystyrene) and carrying a substantial electrical charge.

U.S. Pat. No. 7,465,463 relates to compositions of microspheres having wound healing capacity with anti-inflammatory properties for application to ocular inflammation or injuries, and to methods of use of said composition alone or in combination with other agents in the prevention and treatment of ocular inflammation or injuries. The contents of U.S. Pat. Nos. 5,861,149 and 6,086,863 and 7,465,463 are incorporated by reference herein in their entirety.

Despite the growing number of available therapies, wound healing, such as of chronic and hard to heal wounds remain a rigorous medical, social and economic burden. At present, there is a growing need for therapeutic approaches that promote wound healing. There remains an unmet need for, and it would be highly advantageous to have improved, shelf stable and cost effective compositions for healing a wound.

SUMMARY OF THE INVENTION

The invention provides pharmaceutical compositions for treating a wound, the compositions comprise polystyrene microspheres as an active ingredient. In some embodiments, the composition comprises microspheres a hypotonic solution (e.g., water) as a carrier for the microspheres. In additional embodiments, the compositions comprise an agent (e.g., an excipient) dissolved within the water to form a solution having a specific gravity similar to that of the microspheres. The invention further provides methods for healing a wound in a subject using said compositions, and methods for preparing said compositions.

The present invention is based, in part, on the surprising discovery that polystyrene microspheres suspended in a hypotonic solution are significantly more effective in wound healing than microspheres suspended in saline, an isotonic solution. While saline is considered the standard of care for cleansing, wetting, soaking and hydrating wounds, wound healing was significantly faster when using, a hypotonic solution as a carrier for the microspheres.

As exemplified herein below, full thickness wounds induced in Sprague-Dawley rats were treated with multiple applications of polystyrene microspheres in saline or polystyrene microspheres in distilled water. Unexpectedly, wounds treated with polystyrene microspheres in distilled water reached 50% wound closure significantly faster than wounds treated with polystyrene microspheres suspended in saline.

In additional embodiments, the invention provides improved compositions comprising a thickening agent added to or dissolved within the water to form a carrier solution having a specific gravity substantially similar to the polystyrene microspheres. Without wishing to be bound by any theory or mechanism of action, using a solution having a specific gravity similar to that of the microspheres prevents the aggregation or settling of the microspheres over time, thereby assuring exact and accurate application of the wound healing composition.

According to a first aspect, the invention provides a pharmaceutical composition for treating a wound comprising negatively charged polystyrene microspheres, water and a thickening agent dissolved within the water to form a solution having a specific gravity substantially similar to the polystyrene microspheres. In particular embodiments, the polystyrene microspheres have a specific gravity of about 1.05. In specific embodiments, the thickening agent forms a solution having a specific gravity in the range of 1.02-1.07 grains per cubic centimeter.

Non limiting examples of thickening agents useful in raising the specific gravity of water are selected from the group consisting of: hydrophilic synthetic polymers, sugars or derivatives thereof, glycerol or glycerin their derivatives or combinations thereof. In some embodiments, the hydrophilic synthetic polymer is selected from propylene glycol (PPG) and polyethylene glycol (PEG). In some embodiments, the sugars are selected from the group consisting of sucrose, glucose sorbitol and mannitol. Additional non limiting examples of thickening agents are citric acid and resorcinol. In an exemplified embodiment, the thickening agent is glycerol, or a derivative thereof.

In some embodiments, the thickening agents, constitutes about 1% to about 50% by weight of the composition, about 10% to about 30% by weight of the composition, or about 20% to about 25% by weight of the composition.

According to another aspect, the invention provides a pharmaceutical composition for treating a wound consisting essentially of negatively charged polystyrene microspheres in a hypotonic solution. In some embodiments, said hypotonic solution is water, e.g., distilled water. In an exemplified embodiment, said water is sterile water. In an exemplified embodiment, said water is water for injection (WFI).

In another embodiment, the polystyrene microspheres of the compositions of the invention have a diameter in a range of from about 0.02 μm to about 20 μm. In another embodiment, the polystyrene microspheres have a diameter of about 0.1 μm to about μm or of about 1 μm to about 10 μm.

In yet another embodiment, the polystyrene microspheres constitutes about 0.001% to about 10% by weight of the composition. In a particular embodiment, the plurality of polystyrene microspheres constitutes about 0.001% to about 0.09%, or about 0.025% by weight of the composition.

In particular embodiments, the microspheres of the compositions and methods of the invention form a multi-point contact with a cellular membrane. In another embodiment, said microspheres have negatively charged surface groups. In yet another embodiment, said microspheres are substantially non-biodegradable during the period of treatment.

In another embodiment, the composition is formulated for topical administration onto a wound.

According to another aspect, there is provided a method for treating a wound in a subject in need thereof, the method comprises administering to the subject a therapeutically effective amount of the pharmaceutical compositions of the invention.

According to an additional aspect, there is provided use of a pharmaceutical composition for the preparation of a medicament for treating a wound in a subject in need thereof, the composition comprises negatively charged polystyrene microspheres, water and optionally a thickening agent, said thickening agent forms a solution having a specific gravity substantially similar to the polystyrene microspheres.

According to another aspect, there is provided a pharmaceutical composition for use in treating a wound in a subject in need thereof, the composition comprises negatively charged polystyrene microspheres, water and optionally a thickening agent, said thickening agent forms a solution having a specific gravity substantially similar to the polystyrene microspheres.

In some embodiments, the wound is selected from the group consisting of a burn, a hard (or slow) to heal wound, trauma and a chronic wound. In another embodiment, the chronic wound is selected from the group consisting of diabetic ulcer, a pressure ulcer, an arterial ulcer, a venous ulcer, bed sores associated with long-term disability and pressure ulcers, an acute wound, or a surgical wound. In an additional embodiment, the wound is associated with states in which the normal wound repair ability is weakened.

According to another aspect, there is provided a pharmaceutical composition contained in a package for treating a wound in a subject, the composition comprising 5 about 0.001%-10% by weight of negatively charged polystyrene microspheres suspended in a hypotonic solution. In some embodiments, the hypotonic solution is sterilized water. In additional embodiments, the hypotonic solution is and distilled water. In particular embodiments, said hypotonic solution is WFI. According to yet another embodiment, said hypotonic solution is water, and the pharmaceutical composition further comprises a thickening agent which forms a solution having a specific gravity substantially similar to the polystyrene microspheres.

According to another aspect, there is provided a kit for treating a wound in a subject, the kit comprising (i) a container, (ii) a pharmaceutical composition within the container, and (iii) instructions for applying said pharmaceutical composition to the wound, the pharmaceutical composition comprising about 0.001%-10% by weight of negatively charged polystyrene microspheres suspended in a hypotonic solution. In some embodiments, the hypotonic solution is sterilized water. In additional embodiments, the hypotonic solution is and distilled water. In particular embodiments, said hypotonic solution is WFI. According to yet another embodiment, said hypotonic solution is water, and the pharmaceutical composition further comprises a thickening agent which forms a solution having a specific gravity substantially similar to the polystyrene microspheres.

Other objects, features and advantages of the present invention will become clear from the following description and drawings.

DETAILED DESCRIPTION OF THE INVENTION

The present invention provides, in some embodiments, medical and/or pharmaceutical compositions comprising negatively charges polystyrene microspheres suspended in water. The invention further provides medical or pharmaceutical compositions comprising the polystyrene microspheres and a thickening agent dissolved or dispersed within water to form a solution having a specific gravity substantially similar to said polystyrene microspheres. The present invention further provides methods for healing a wound in a subject using said compositions, methods for preparing same and kits comprising said compositions.

As exemplified herein below, full thickness wounds induced in Sprague-Dawley rats were treated with multiple applications of polystyrene microspheres in saline or polystyrene microspheres in water for injection (WFI). Unexpectedly, polystyrene microspheres in WFI treated wounds reached 50% wound closure significantly faster than wounds treated with polystyrene microspheres in saline.

Thus, in some embodiments of the present invention, the microspheres are suspended or dispersed in water. By virtue of using water as the carrier of the microspheres, the compositions are easily sterilized and may be kept at room temperature (i.e., do not require refrigeration). In some embodiments, the compositions are advantageous for use by subjects demonstrating hyper-sensitivity to therapeutic compositions, such as the compositions described in International Patent Application Publication Nos. WO 98/055108 and WO 00/024378.

In some embodiments, the invention provides a pharmaceutical or medical composition for treating a wound comprising or consisting of negatively charged polystyrene microspheres and water. In additional embodiments, the compositions of the invention further comprise an excipient (e.g., a water soluble thickening agent) added to or dissolved within the water to form a solution having a specific gravity substantially similar to that of the microspheres. In some embodiments, the thickening agent is dispersed in the water to form a dispersion having a specific gravity substantially similar to the polystyrene microspheres.

In some embodiments, the microspheres remain in suspension or dispersion over a long period of time when using a solution having a specific gravity substantially similar to that of the microspheres. Use of said improved compositions assures the accurate application of the wound healing composition. For instance, the essential step of mixing the composition prior to its application to the wound (to assure the microspheres are suspended/dispersed) may be avoidable, which is particularly advantageous in a large portion of subjects having chronic wounds, such as elderly subjects.

In an exemplified embodiment, there is provided a pharmaceutical composition comprising (i) about 0.001%-10% by weight of negatively charged polystyrene microspheres, (ii) about 10%-30% by weight of glycerol, glycerin, a combination or a derivative thereof, and (iii) water as a carrier for said microspheres.

According to certain embodiments, there is provided a method for preparing the compositions of the present invention. In some embodiments, the method comprises the following general steps: adding a thickening agent to a hypotonic solution (e.g., distilled water or WFI) to form a solution having a specific gravity substantially similar to microspheres (e.g., in the range of 1.02 and 1.07); and adding said negatively charged microspheres to the solution.

In some embodiments, the carrier solution is prepared and then the microspheres are added to the solution. In other embodiments, the microspheres are added to the solution prior to adjustment of the specific gravity of the solution. Preferably, the specific gravity of the carrier solution is adjusted and optionally inspected, prior to, and/or after the addition of the microspheres. A skilled artisan will appreciate that depending on the type of thickening agent various mixing time frames are required for the preparation of the carrier solution. In non-limiting embodiments, the thickening agent is added and mixed for at-least 5 min, at-least 10 min, at-least 15 min, at-least 20 min, at-least 30 min or at-least 60 min, prior to the addition of the microspheres.

In particular embodiments, the composition of the invention has a pH of about 4 to about 8, about 4.5 to about 7.5, or about 5 to about 7. In one embodiment, said composition has a pH of about 4.5 to about 5.5 (e.g., 5). In another embodiment, said composition has a pH of about to about 6.5 to 7.5 (e.g., 7).

Typically, the water used in the compositions and methods of the invention is sterilized water. In some embodiments, the water is distilled water. In an exemplified embodiment, said water is water for injection (WFI).

Water for Injection (WFI) is known in the art as sterile, nonpyrogenic, distilled water commercially available in a single dose container for intravenous administration after addition of a suitable solute. The pH of WFI is 5.5 (5.0 to 7.0) and the osmolarity is 0.

A "saline solution" is known in the art as a sodium chloride solution obtained by dissolving about 9 grams of sodium chloride (NaCl) in 1 liter of distilled water.

As used herein, the terms "hypotonic", "isotonic" and "hypertonic" relate to a concentration relative to the solute concentration in the cytoplasm of a cell.

Specific Gravity

Specific gravity is an expression of the weight of a substance relative to the weight of an equal volume of water. Typically, the specific gravity is measured in 25° C. For example, water has a specific gravity of one. In some embodiments of the invention, a thickening agent is dissolved within the water carrier to form a solution having a suitable specific gravity. In particular embodiments, a suitable specific gravity is similar to that of the microspheres within the compositions of the invention. The specific gravity of polystyrene microspheres is normally in the range of 1.05. In particular embodiments, the water soluble thickening agent has a solution-stabilizing effect. The term "solution-stabilizing effect" refers to the microspheres remaining in suspension/dispersion (i.e., not aggregating) over a substantially long period of time. A "substantially long period of time" as used herein relates to a time period of at least 10%, at least 15%, at least 20%, at least 30%, at least 40% or at least 50% longer than the compositions comprising microspheres which are devoid of a thickening agent. As disclosed herein, said solution-stabilizing effect is kept for at least three months.

In some embodiments, a sufficient amount of a solvent a water soluble thickening agent) is dissolved within the water such that the solution has a specific gravity between 1.02 and 1.07, particularly between 1.03 and 1.06, more particularly between 1.04 and 1.06. The thickening agent is any item capable of modifying the specific gravity of the solution to be substantially similar to that of the microspheres within the composition. Suitable agents include organic solvents and salts. Suitable organic solvents for increasing the specific gravity of water include glycols, such as ethylene glycol, propylene glycol, polyethylene glycol and polypropylene glycol.

Non-limiting examples of thickening agents and their specific gravity are: glycerol (1.129 at 25° C.), propylene glycol (1.036 at 25° C.), citric acid (1.665 at 25° C.), glycerin (1.263 at 25° C.), glycerin 50% water (1.13 at 20° C.), resorcinol (1.272 at 25° C.), PEG 300 (1.12-1.13 at 25° C.), molasses (1.40-1.49 at 15.6° C.), corn syrup selected from 86.4 Brix, 84.4 Brix and 78.4 Brix (1.405-1.459 at 15.6° C.), sucrose selected from 60 Brix, 64 Brix, 68 Brix, 72 Brix, 74 Brix, 76 Brix (1.29-1.39 at 15.6° C.); glucose (1.35-1.44 at 15.6° C.), sorbitol (1.29 at 20° C.), mannitol (1.50 at 25° C.), mannitol 20% in water (0.965-1.070 at 25° C.), and meltodextrin (2.95 at 25° C.).

Further, the thickening agent is present in the composition in a suitable volume to generate a specific gravity within the desired ranges (e.g., substantially similar to that of the microspheres). As a non-limiting example, the thickening agent is approximately 0.75 to 75.0 percent, 1 to 50 percent, 10 to 35 percent, alternatively 15 to 25 percent, by volume, of the solution. In some embodiments, the thickening agent is at least 1, at least 5, at least 10, at least 15, at least 16, at least 17, at least 18, at least 19, at least 20 percent by volume, of the solution. In another embodiment, the thickening agent is at most 50, at most 40, at most 35, at most 34, at most 33, at most 32, at most 31, at most 30, at most 29, at most 28, at most 27, at most 26, at most 25 percent by volume, of the solution. In an exemplified embodiment, the thickening agent (e.g., glycerol) is about 22 percent by volume, of the solution.

In additional embodiments, the thickening agent does not interfere with the capability of the microspheres within the composition to form a multi-point contact with a 5 cellular membrane. In yet another embodiment, the thickening agent does not interfere with the negative charge of said microspheres. In specific embodiments, the thickening agent is nonionic.

In some embodiments, the specific gravity of the carrier is within 0.04 of the specific gravity of the microspheres. In another embodiment, the specific gravity of the carrier is within 0.03 of the specific gravity of the microspheres. In another embodiment, the specific gravity of the carrier is within 0.02 of the specific gravity of the microspheres. In yet another embodiment, the specific gravity of the carrier is within 0.01 of the specific gravity of the microspheres. A specific gravity within "X" refers to an interval extending from minus X to plus X of the referenced specific gravity.

As used herein the terms "substantially similar", "substantially identical" or "substantially equal" with respect to the specific gravity of the polystyrene microspheres, refers to the alteration of the specific gravity of the carrier to resemble the specific gravity the microspheres, so that the microspheres remain in suspension or dispersion for longer period of times (compared to an unaltered carrier). For instance, a substantially similar specific gravity relates to an interval extending from minus 0.04 of the referenced specific gravity to plus 0.04 of the referenced specific gravity, or to an interval extending from minus 0.03 of the referenced specific gravity to plus 0.03 of the referenced specific gravity, alternatively to an interval extending from minus 0.02 of the referenced specific gravity to plus 0.02 of the referenced specific gravity.

Microspheres

The microspheres within the compositions of the invention are able to promote wound healing without the further addition or inclusion of any drug or other therapeutic substance. Said microspheres do not degrade or undergo other chemical alteration in order to produce their therapeutic effect, and are considered the active ingredient in the compositions of the present invention, rather than acting merely as a carrier for another, different active ingredient.

In one embodiment, the microspheres of the invention form a multi-point contact with a cellular membrane, such as the outer cell membrane. In another embodiment, said microspheres are substantially non-biodegradable during the period of treatment (i.e., until 5 the wound is essentially healed). In yet another embodiment, said microspheres promote wound healing without significant chemical alteration or degradation. The microspheres are substantially insoluble in aqueous media, and form a suspension or dispersion in such media.

In another embodiment, said microspheres have negatively charged surface groups. Typically, the overall charge carried by microspheres may be measured as a Z or zeta potential, such as by electrophoretic mobility (millivolts) by a ZetaMaster (Malvern Instruments, United Kingdom). In some embodiments, the term "charged" refers to a Z potential with a value of at least about −1 mV, of at least about −10 mV, or of at least about −20 mV. In other embodiments, the negative charge ranges from about −30 mV to about −80 mV.

The structure of these microspheres includes a core and at least one type of charged surface group which is present at least on the exterior of the core of the microsphere. Examples of suitable materials for the core include but are not limited to long chain polymers such as polystyrene, derivatized polystyrene, latex, poly-β-alanine, polylysine, poly-N-ethyl-4-vinylpyridinium bromide, polymethylacrylate (PMMA) and silicone. Preferably, the material is selected from the group consisting of polystyrene and derivatized polystyrene. Examples of surface groups include but are not limited to sulfate, poly-N-ethyl-4-vinylpyridinium bromide, protamine, protamine sulfate, protamine salts, polylysine, carboxyl, polystyrene and derivatized polystyrene. More preferably, the surface group is selected from the group consisting of polystyrene, derivatized polystyrene, polylysine and carboxyl. These surface groups may be present as part of the core of the microsphere, or may be added later by such chemical processes as derivatization of the long-chain polymer. Hereinafter the term "derivatization" refers to the process of chemically altering, modifying or changing a molecule or a portion thereof.

Thus, the structure of the microspheres includes a "core" and a "surface group", which are two separate elements, even though the list of possible species of each of these elements overlaps. For example, polystyrene can be both a surface group and a core material of the microsphere.

It will be appreciated to those skilled in the art that these microspheres, more generally described as "agents", can be beads, particles or globules which are either solid or hollow. The shape of the agents can be regular, such as spherical or elliptical, or regular non-spherical shapes; or the shape of the particles can be non-regular, so that the surface is not a single continuous curve or so that the surface is not smooth. Furthermore, the agents can be a mixture of different polymers and can also be a mixture of different particles, beads or globules of different sizes. The agents can also have pores of different sizes.

In particular embodiments, the microspheres of the invention are made of polystyrene, either with carboxyl or amino surface groups or without additional surface groups.

Therapeutic Use

In particular embodiments, the pharmaceutical compositions of the present invention are useful for treating a wound in a subject in need thereof.

A wide variety of wounds can be treated with the composition of the invention including, but not limited to, full and partial thickness burn wounds, sunburns, frostbite; ulcerative lesions such as pressure (decubitus) ulcers and varicose, stasis and trophic ulcers; wounds associated with surgical procedures such as amputation, incision, circumcision and episiotomy; traumatic and pyogenic wounds; vaginitis; cervicitis; pilonidal cyst wounds; pathological fissure and pathological hemorrhoids.

According to certain embodiments, the wounds are associated with states in which the normal wound repair ability is weakened. According to typical embodiments, the wounds are associated with states such as diabetes and/or occur in patients in their older age or during steroid treatment or chemotherapy. According to typical embodiments, the wound is selected from the group consisting of diabetic foot ulcers, neuropathic ulcers including neuropathic forefoot ulcers, burns, diabetic pressure ulcers or diabetic venous ulcers; bed sores or pressure ulcers associated with long-term disability, each representing a separate embodiment of the present invention.

Anatomically, the tissues which can be treated with the present invention include, but are not limited to, skin and muscle. The term "subject" refers to in particular embodiments to a mammal, preferably a human.

The method of the present invention may also be used cosmetically, such as to prevent excess scar formation in a cut or other wound to the skin such as the skin of the face, and to treat acne. In a cosmetic sense, the term "excess scar formation" includes any scarring which is cosmetically undesirable or unacceptable.

As used herein, the term "burn" refers to an injury to tissues caused by heat, cold, chemicals, electricity, or irradiation effects.

The term "chronic wounds" or "hard to heal wounds" as used herein refers to clinical conditions having characteristic symptoms wherein the wounds do not heal for a prolonged time and may have a tendency to recurrence. The chronic wounds usually are associated with states in which the normal wound healing ability is weakened, such as diabetes, patients in their older age, patients with limited ability of movement, or patients during steroid treatment or chemotherapy. Thus, patients with such badly healing wounds are typically those suffering from diabetic ulcers, including diabetic foot ulcers, diabetic neuropathic ulcers, including neuropathic forefoot ulcers, diabetic pressure ulcers or diabetic venous ulcers, as well as patients with limited movement ability suffering from bed sores. Bed sores usually affect peoples who stay in one place for prolonged time for any reason.

As used herein, the terms "severity of the burn" or "severity of the wound" refer to one or more parameters used to classify the burn or wound, such as the degree of burn/wound, the percentage of the total body surface area affected by the burn/wound and the depth of the burn/wound.

The severity of a wound or a burn is typically classified into stages and degrees, respectively.

Stage one wounds do not have any visible skins cuts. However, the skin covering the wound can be remarkably different from the surrounding area. The differences may be changes in temperature, firmness, or color of the skin. The wound may also be painful or itchy. In a Stage two wound the top most layers of skin is severed (epidermis and dermis). There may be some drainage. Stage three wounds are deeper than stage 2 wounds. They typically go down to the "fat" layer (subcutaneous), but do not extend any further. There may be dead tissue and drainage. Stage four wounds are very serious. These wounds are characterized by going as far down as the bone and muscle. Dead tissue and drainage are almost always present. Often, at this stage, the wound is also infected.

First degree burns result in some redness and swelling of the injured part, without necrosis of any tissue or the formation of blisters. Second degree burns show a variable destruction of parts of the dermis so that blistering occurs. Healing by regeneration in such superficial burns does not necessitate skin grafting, unless secondary infections ensue. Third degree burns are marked by complete destruction of a skin region, including the necrosis of accessory skin structures such as hair and sweat glands. A brownish-black eschar (a dry scab or slough) marks the destroyed tissue. In deep third degree burns, also classified as fourth degree burns, tissue is destroyed to the level of or below the deep fascia lying beneath the subcutaneous fat and connective tissue of the body. Muscle, bone, deeper nerves, and even organs may be injured or destroyed by this severe degree of burn.

In some embodiments, the compositions of the invention are capable of treating cutaneous and subcutaneous wounds.

The composition amount and administering regimen will be set according to the burn or wound type and severity and parameters of the subject including age, gender and general health as measured by a skilled practitioner and established to be safe and effective in clinical trials.

According to certain embodiments, the compositions are applied to the treated area on a once to twice daily regimen. According to additional embodiments, the compositions are applied to the treated area every other day, or twice a week. The number of repeated administrations would depend on the severity of the initial wound.

The term "pharmaceutically acceptable" means approved by a regulatory agency of the Federal or a state government or listed in the U.S. Pharmacopeia, EU Pharmacopeia or other generally recognized pharmacopeia for use in animals, and more particularly in humans. The term "carrier" refers to a diluent, excipient, or vehicle with which the microsphere is administered. Carriers are more or less inert substances when added to a formulation to confer suitable consistency or form to the formulation.

The terms "effective amount" as used in connection with the compositions of the present invention refer to an amount of the composition that is sufficient to achieve an intended wound healing effect. Thus, "an effective amount" refers to a non-toxic, but sufficient amount of the composition to achieve therapeutic results in treating a burn or a wound as described herein. Various biological factors and the carrier characteristic may affect the ability of a substance to perform its intended task. Therefore, an "effective amount" or a "therapeutically effective amount" may depend on such biological factors. The determination of an effective amount is well within the ordinary skill in the art of medical device, pharmaceutical, nutraceuticai, herbaceutical, and health sciences. See, for example, Meiner and Tonascia, "Clinical Trials: Design, Conduct, and Analysis," Monographs in Epidemiology and Biostatistics, Vol. 8 (1986). According to certain aspects of the invention, the term "therapeutic effective amount" refers to the amount capable of promoting the healing of a wound or a burn, up to complete healing of the skin tissues.

As used herein the terms "about", "similar" or "approximately", placed before a numerical value "X", refers to an interval extending from X minus 10% of X to X plus 10% of X, and preferably to an interval extending from X minus 5% of X to X plus 5% of X.

Concentrations, amounts, ratios, and other numerical data may be expressed or presented herein in a single number or a range format. It is to be understood that the range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited.

The following examples are presented in order to more fully illustrate some embodiments of the invention. They should, in no way be construed, however, as limiting the broad scope of the invention.

EXAMPLES

Materials and Methods

Animals

11 Sprague-Dawley rats (female, 250-300 g, Harlan Laboratories, Jerusalem, Israel) 5

Test Article 0.025% polystyrene microspheres in Water For Injection (WFI).

Materials

Anesthesia Cocktail: a mixture of: 1 mL Ketamin (100 mg/ml, Fort Dodge Animal Health, Fort Dodge, USA), 1 mL Xylazine (20 mg/ml, Europet), and 13 mL of NaCl 0.9%.

Analgesia: Buprinorphine (0.3 mg/ml, VetMarket, Petach-Tikva, Israel) 3.3 ml of Buprinorphine was diluted in 1 liter of drinking water.

0.025% polystyrene beads in saline. Treatment solutions were supplied in the same white, polypropylene, ear-dropper 15 mL container.

Wound Incision

Rats were numbered and placed in separated cages and given free access to food and water. The rats were anesthetized for the dressing changes.

The dorsum of anesthetized rats was shaven and sterilized with EtOH (70%). The skin was stretched and marked for two wounds measuring 1×2 cm on the dorsal side of the rat. Using scalpel and scissors full thickness wounds were incised, extending to the muscle fascia (not including).

The right and the left wounds of each rat were treated with coded solution (4 drops to fully cover the wound area). The wounds were dressed. During the experiment the rats were given analgesia in their drinking water (Buprinorphine).

Wound Treatment

After each removal of dressing, photos of the wounds were taken on Day 0 and in every other day.

Wounds area was measured using image analysis software. The rate of wound healing of each wound was calculated by the equation:

$$\frac{\text{Area } t_0 - \text{Area } t_x}{\text{Area } t_0} \times 100$$

where: (area $t_0$=original area of the wound, $t_x$=time from wounding).

Example 1

Wound Closure Rate of Wounds Treated with Polystyrene Microspheres in Water for Injection (WFI) or with Saline Wound closure rate of wounds treated with saline or microspheres in saline was compared to wounds that were treated with polystyrene microspheres in WFI. The experiment was carried out at the Soroka Medical Center according to the procedures detailed above.

Wound Healing Test (Closure Rate)

Rats were anesthetized and full thickness wounds were produced on their dorsal side (day 0). On each animal 5 μm polystyrene negatively charged microspheres suspended in WFI was applied on the left wound and saline was applied on the right wound. In a second test set, 5 μm polystyrene microspheres suspended in saline was applied on the left wound and 5 μm polystyrene microspheres suspended in WFI was applied on the right wound. The wounds were dressed with gauze, Kerlex roll, and dressing net. The rats were anesthetized, photographed, treated and dressed every other day. X indicates rat expired.

Figure 1:
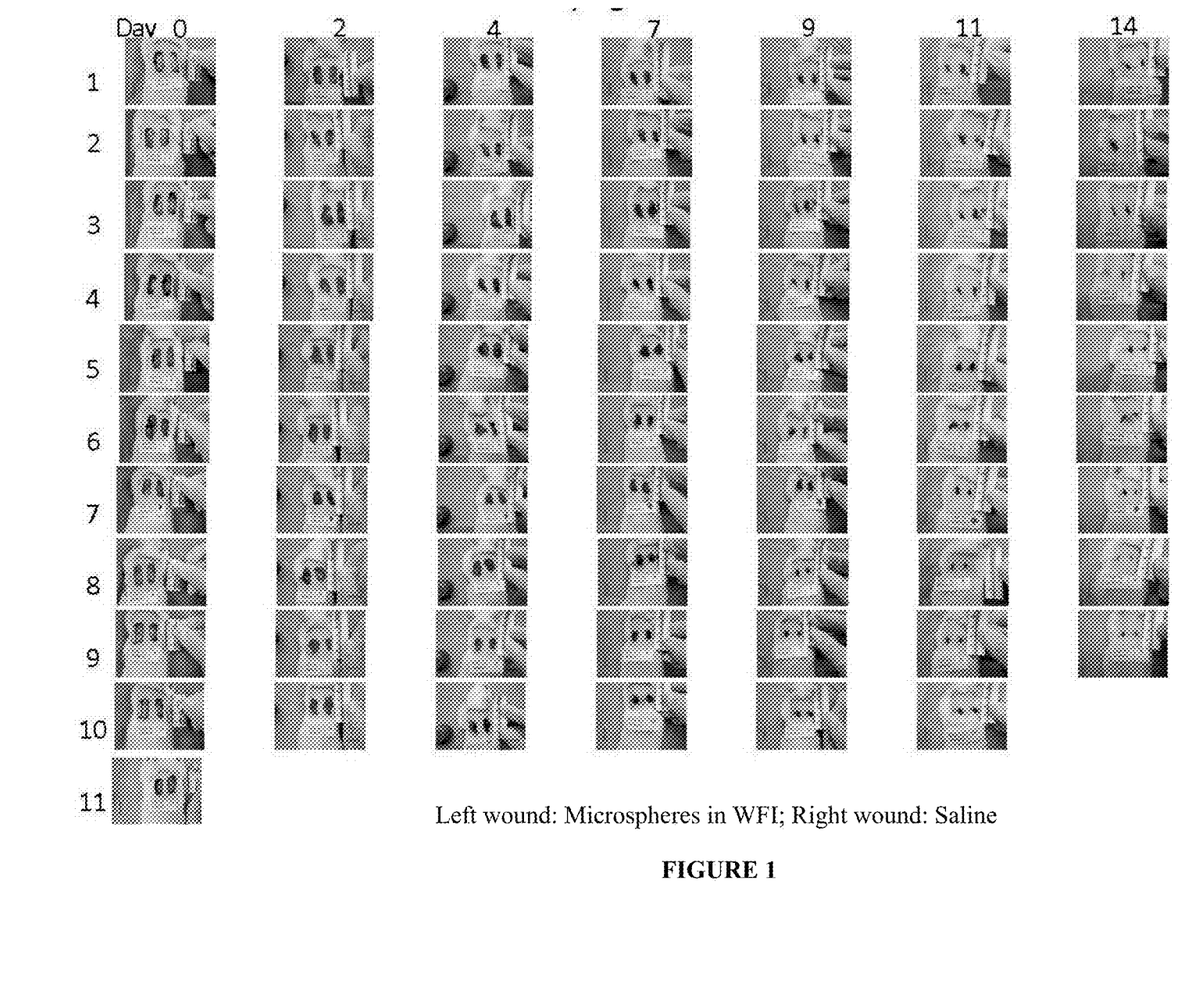
FIG. 1 depicts the wound healing effect of polystyrene microspheres in Water for Injection (WFI) compared to saline. Rats were anesthetized and full thickness wounds were produced on their dorsal side (day 0). On each animal polystyrene microspheres in WFI was applied on the left wound and saline was applied on the right wound. The wounds were then dressed with gauze. The rats were anesthetized, photographed, treated and dressed on days 0, 2, 4, 7, 9, 11 and 14.
Figure 2A:
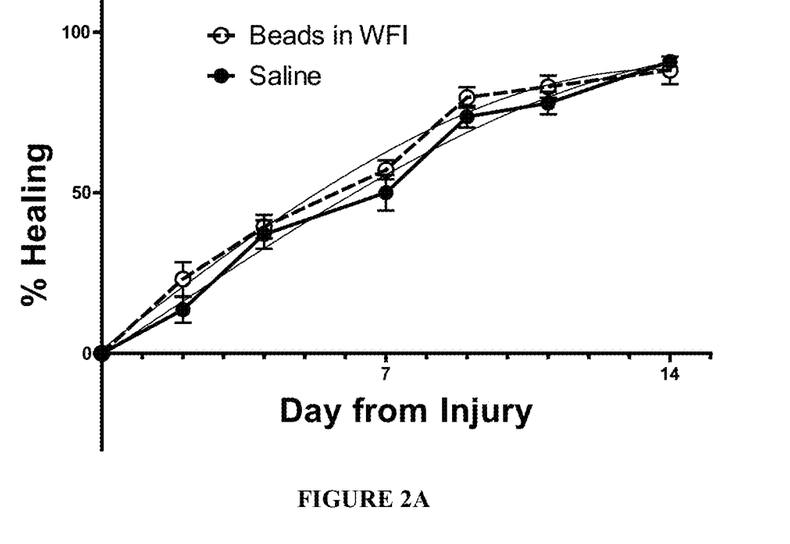
FIG. 2A is a graph showing wound healing kinetics of polystyrene microspheres in WFI (dashed line) compared to saline (straight line).

FIG. 1 shows the follow up of wound closure up to day 14. FIG. 2A presents the comparison of the healing kinetics of polystyrene microspheres in WFI and saline treated wounds. Mean 50% healing time was calculated by extrapolation from the non-linear regression (third order polynomial) fit graph (dashed lines) using Prism 5 software. Saline treated wounds reached 50% wound closure at day 6.23 (95% CI, 5.59-6.84), while polystyrene beads in WFI treated wounds, reached 50% wound closure at day 5.31 (95% CI, 4.71-5.89). The difference is statistically significant p=0.0476 (paired t-test) or p=0.0476 (sign rank test).

Figure 2B:
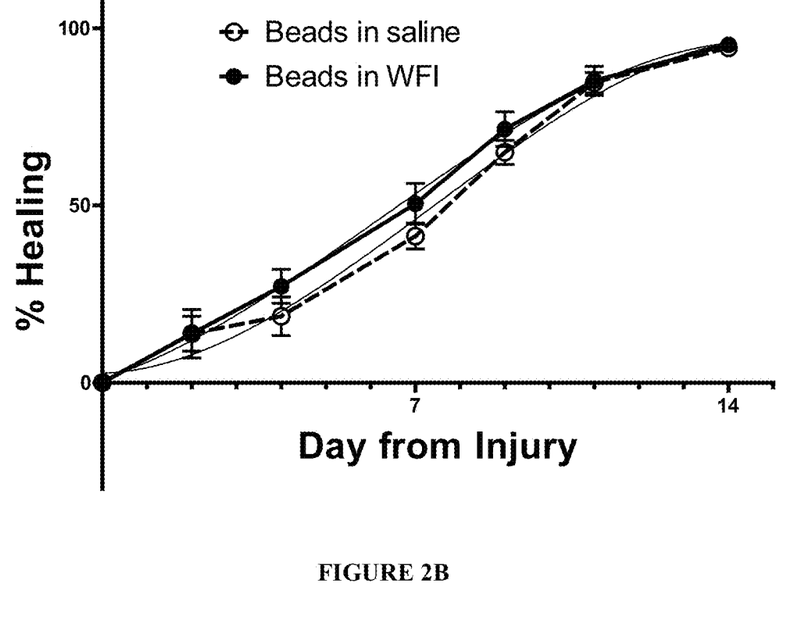
FIG. 2B is a graph showing wound healing kinetics of polystyrene microspheres in WFI (straight line) compared to microspheres in saline (dashed line).

FIG. 2B presents the comparison of the healing kinetics of polystyrene microspheres in WFI compared to microspheres in saline. Wounds treated with polystyrene microspheres in WFI reached 50% wound closure at day 6.62 (95% CI, 6.01-7.21), while polystyrene microspheres in saline treated wounds, reached 50% wound closure at day 7.42 (95% CI, 6.97-7.88).

Example 1 shows that unexpectedly polystyrene microspheres suspended in WFI demonstrate significant higher activity in wound closure compared with microspheres suspended in saline or saline alone that is considered the standard of care in treating and cleansing wounds.

Example 2

In Vivo Assessment of Wound Closure Rate Following Applications of the Polystyrene Microspheres in Water Based Formulations The aim of this study was to evaluate the wound closure rate following multiple applications polystyrene microspheres (0.025%) suspended in WFI and 22% glycerol in 3 separate formulations: (i) formulation without pH adjustment; (ii) formulation adjusted to pH 5; and (iii) formulation adjusted to pH 7. Formulations comprising polystyrene negatively charged microspheres (5 μm), suspended in Dulbecco's Modified Eagle's Medium (DMEM) was used as a positive control.

Prior of conducting the studies, the formulations were tested for stability and were found to be stable for at least 3 months without showing neither microspheres aggregation nor sedimentation. In addition, no significant pH changes were observed during that period of time.

Full thickness wounds induced in Sprague-Dawley rats were treated with multiple applications of saline or polystyrene beads in WFI. Wound closure was followed up to day 14. The rate of wound healing was calculated as % difference from the original wound area.

Figure 3:
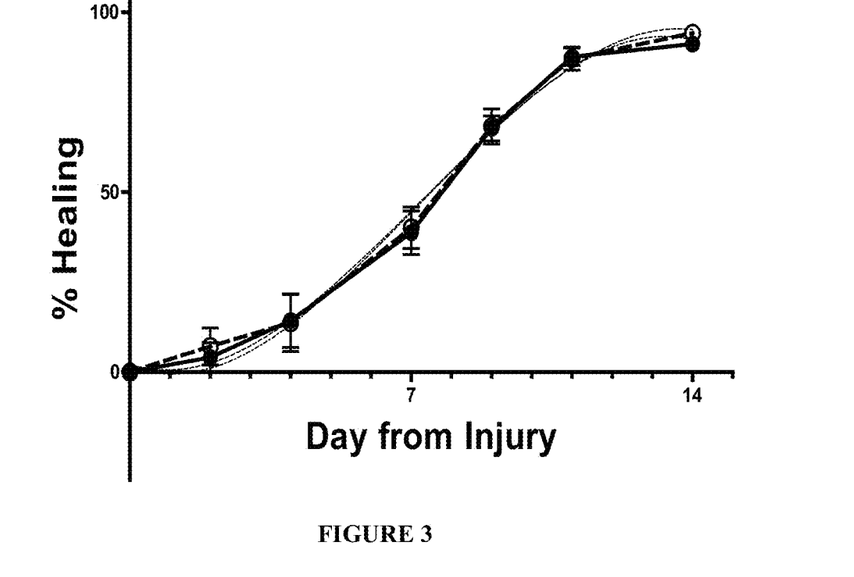
FIG. 3 is a graph showing wound healing kinetics of polystyrene microspheres suspended in WFI and 22% glycerol (dashed line) compared to microspheres in DMEM (straight line).

Formulation (i) comprising polystyrene beads in WFI and 22% glycerol reached 50% wound closure at day 7.47 (95% CI, 6.98-7.97), while the wounds treated with the control formulation reached 50% wound closure at day 7.50 (95% CI, 7.07-7.94) (FIG. 3). This result shows that polystyrene microspheres suspended in WFI and 22% glycerol exhibit identical efficacy in wound closure compared with the positive control.

Figure 4:
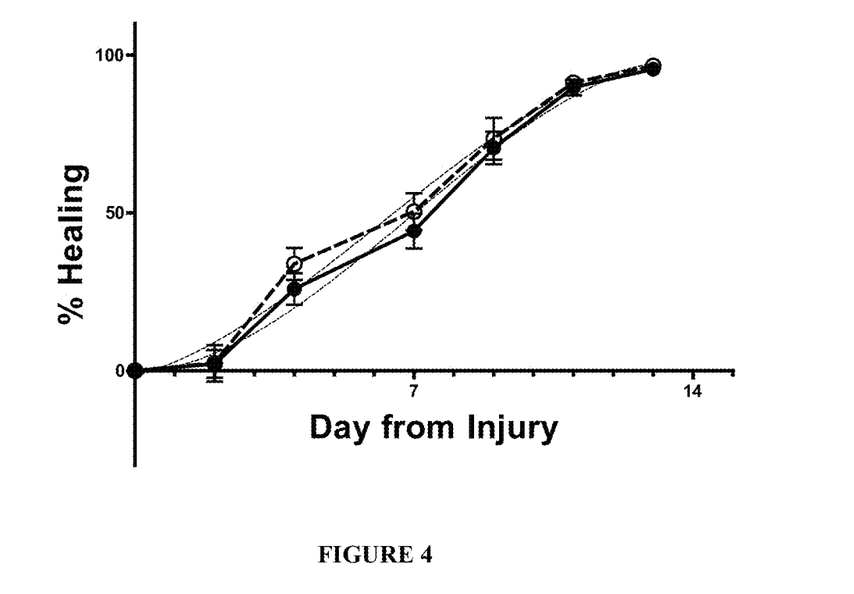
FIG. 4 is a graph showing wound healing kinetics of polystyrene microspheres suspended in WFI and 22% glycerol (pH 5) (shown using a dashed line) compared to microspheres in DMEM (straight line).

Formulation (ii) comprising polystyrene beads in WFI and 22% glycerol (pH 5) reached 50% wound closure at day 6.5 (95% CI, 5.93-7.06), while the control treated wounds reached 50% wound closure at day 7.03 (95% CI, 6.57-7.50) (FIG. 4). According to the statistics the difference is statistically significant p=0.048 (paired t-test). This result indicates that polystyrene microspheres suspended in WFI and 22% glycerol at pH 5 exhibit superior efficacy in wound closure over polystyrene microspheres suspended in DMEM.

Figure 5:
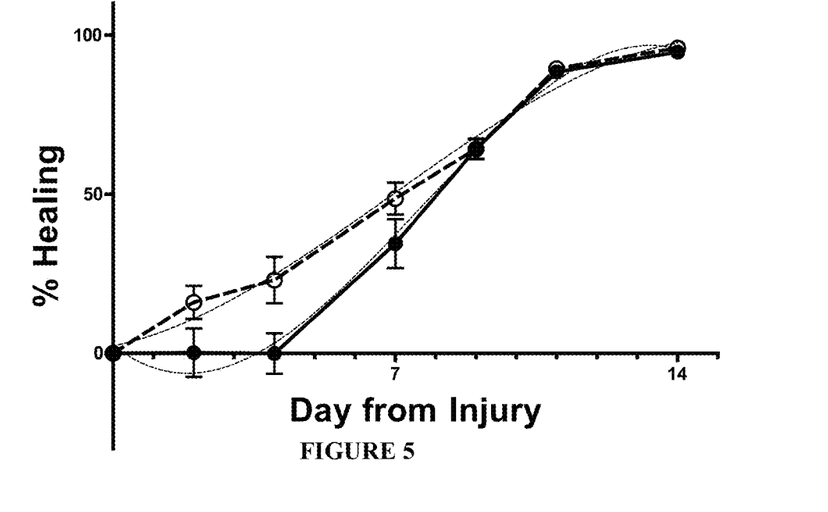
FIG. 5 is a graph showing wound healing kinetics of polystyrene microspheres suspended in WFI and 22% glycerol (pH 7) (shown using a dashed line) compared to microspheres in DMEM (straight line).

Formulation (iii) comprising polystyrene beads in WFI and 22% glycerol (pH 7) reached 50% wound closure at day 6.95 (95% CI, 6.38-7.50), while the control treated wounds reached 50% wound closure at day 7.95 (95% CI, 7.51-8.41) (FIG. 5). According to the statistics the difference is not statistically significance p=0.0720 (paired t-test). This result indicates that polystyrene microspheres suspended in WFI and 22% glycerol at pH 7 exhibit similar efficacy in wound closure compared with polystyrene microspheres suspended in DMEM.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A pharmaceutical composition for treating a wound comprising negatively charged polystyrene microspheres, water, and a thickening agent, wherein the thickening agent forms a solution having a specific gravity in the range of 1.02-1.07, the specific gravity being substantially similar to specific gravity of the polystyrene microspheres.

2. The pharmaceutical composition of claim 1, wherein the thickening agent is selected from the group consisting of: hydrophilic synthetic polymers, sugars, glycerol, propylene glycol (PPG), derivatives thereof, and combinations thereof.

3. The pharmaceutical composition of claim 2, wherein the hydrophilic synthetic polymer is polyethylene glycol (PEG).

4. The pharmaceutical composition of claim 2, wherein the sugars or derivatives thereof are selected from the group consisting of sucrose, glucose, sorbitol and mannitol.

5. The pharmaceutical composition of claim 2, wherein the thickening agent is glycerol.

6. The composition of claim 1, wherein the concentration of the thickening agent constitutes about 1% to about 50% by weight of the composition.

7. The pharmaceutical composition of claim 1, wherein the polystyrene microspheres have a diameter in a range of from about 0.02 μm to about 20 μm.

8. The pharmaceutical composition of claim 1, wherein the polystyrene microspheres constitute about 0.001% to about 10% by weight of the composition.

9. The pharmaceutical composition of claim 1, wherein the polystyrene microspheres are non-biodegradable during the period of treatment.

10. The pharmaceutical composition of claim 1, wherein the composition has a pH from about 4.5 to about 7.5.

11. A method for treating a wound comprising administering to a subject in need of such treatment the pharmaceutical composition of claim 1.

12. The method of claim 11, wherein the wound is selected from the group consisting of a burn, trauma, hard to heal and a chronic wound.

13. The method of claim 12, wherein the chronic wound is selected from the group consisting of diabetic ulcer, a pressure ulcer, an arterial ulcer, a venous ulcer, an acute wound, post traumatic and a surgical wound.

14. The pharmaceutical composition of claim 1, wherein the thickening agent forms a solution having a specific gravity in the range of 1.04-1.06.

15. The pharmaceutical composition of claim 14, wherein the thickening agent forms a solution having a specific gravity of about 1.05.

16. The pharmaceutical composition of claim 1, wherein the thickening agent is glycerol.

17. The pharmaceutical composition of claim 16, wherein glycerol present in an amount of about 20% to about 25% by weight of the composition forms a solution having a specific gravity of about 1.05.

* * * * *